United States Patent [19]

Bouchette

[11] Patent Number: 4,772,492
[45] Date of Patent: Sep. 20, 1988

[54] BINDER CATALYST FOR AN ANTIMICROBIALLY ACTIVE, NON-WOVEN WEB

[75] Inventor: Michael P. Bouchette, Appleton, Wis.

[73] Assignee: James River Corporation, Richmond, Va.

[21] Appl. No.: 139,825

[22] Filed: Dec. 30, 1987

Related U.S. Application Data

[62] Division of Ser. No. 925,258, Oct. 31, 1986, Pat. No. 4,737,405, which is a division of Ser. No. 781,413, Sep. 30, 1985, Pat. No. 4,740,398.

[51] Int. Cl.$^4$ .............................................. B05D 1/36
[52] U.S. Cl. ................................. 427/342; 427/389.9; 427/391; 427/392; 427/411; 427/412
[58] Field of Search ............ 427/342, 391, 411, 389.9, 427/392, 412

[56] References Cited

U.S. PATENT DOCUMENTS 4,737,405  4/1988  Bouchette ........................... 427/342
4,740,398  4/1988  Bouchette ........................... 427/342

*Primary Examiner*—James C. Cannon
*Attorney, Agent, or Firm*—Finnegan, Henderson, Farabow, Garrett & Dunner

[57] ABSTRACT

An antimicrobially active, non-woven web, a wet wiper containing the web, and a method of making the web. The method includes the steps of forming an unbonded fibrous web; applying throughout the unbonded fibrous web an uncured polymeric binder; applying a leachable catalyst to catalyze the cross-linking of the binder during curing, the leachable catalyst being antimicrobial; and curing the binder to cross-link the binder and bind the fibers together to form an antimicrobially active, non-woven web.

11 Claims, No Drawings

BINDER CATALYST FOR AN ANTIMICROBIALLY ACTIVE, NON-WOVEN WEB

This is a division of application Ser. No. 925,258 filed Oct. 31, 1986 and now U.S. Pat. No. 4,737,405 which is a division of application Ser. No. 781,413 filed Sept. 30, 1985 and now U.S. Pat. No. 4,740,398.

BACKGROUND OF THE INVENTION

The present invention relates to non-woven webs and, more particularly, to antimicrobially active, air-laid, non-woven webs, to wet wipers containing such a web, and to a method of making the web.

Wet wiper products, including those utilizing non-woven and air laid webs, require antimicrobial properties to destroy or inhibit the growth of various microorganisms, bacteria, yeasts, and molds. Typically, the antimicrobial agent or agents are incorporated in the liquid or lotion phase of the wet wiper product. In this manner, the antimicrobial agent is able to penetrate throughout the entire wiper product and, thus, provide a sort of homogeneous antimicrobial efficacy.

The non-woven webs used in wet wiper products also usually contain a polymeric binder and a catalyst to aid in the crosslinking of the binder to develop sufficient wet strength in the web. Unfortunately, when the product is ultimately used, the catalysts can leach out into the lotion phase of the wiper and thereby rub-off, thus leaving an irritating residue on the skin of the user. Many individuals exhibit adverse reactions to such residues and, hence, their enjoyable use of the non-woven web and wet wiper product is significantly impeded.

Although organic acids have been used in non-woven webs to catalyze the cross-linking of the binders present in the non-woven webs, the art has failed to recognize that these chemicals can be selected not only to act as a binder catalyst, but also to possess antimicrobial properties. For example, U.S. Pat. No. 3,922,462 to Katz uses oxalic, dichloroacetic, and paratoluenesulfonic acids to catalyze a binder in a web. These acids, however, are toxic upon ingestion or inhalation, as well as being a skin irritant. Hence, when these acids leach from the web, instead of providing a beneficial effect, they pose significant health and safety hazards.

Thus, these wiper products require an antimicrobial agent, in addition to the catalyst and binder, to impart antimicrobial properties to the web. The need for a separate antimicrobial agent adds time and cost to the process of making the product. For example, when an antimicrobial agent is presently added to the non-woven web in an off-line process after the non-woven web product has been formed, the cost of producing the wet wiper product is increased.

In sum, present wet wiper products that exhibit antimicrobial activity are less than satisfactory. Often, the webs contain binder catalysts that are toxic and leave an irritating residue on the user's skin. If these undesirable properties are avoided by removing the catalyst after the binder cure but before the web is used, time and cost are added to the process of making the web.

SUMMARY OF THE INVENTION

The inventor of the present invention has developed an anti-microbially active, non-woven web that overcomes the significant and inherent disadvantages present in previous non-woven webs that attempt to exhibit antimicrobial properties. Unlike previous webs, the non-woven web of the present invention does not contain a toxic and irritating binder catalyst that poses health and safety hazards during the use of the web. Additionally, by using the binder catalyst to impart the antimicrobial properties to the web, the present invention eliminates the need for a separate antimicrobial agent to be added to the non-woven web.

The present invention achieves these various advantages by providing a method for making an antimicrobially active, non-woven web. The method comprises the steps of: (a) forming an unbonded cellulosic fiber web; (b) applying throughout the unbonded cellulosic fiber web an uncured polymeric binder; (c) applying a leachable catalyst to the web to catalyze the cross-linking of the binder during curing, the leachable catalyst being antimicrobial; and (d) curing the binder to cross-link the binder and bind the cellulosic fibers together to form an antimicrobially active, non-woven web. Preferably, the leachable catalyst is an organic acid selected from the group consisting of malic acid, citric acid, ethylenediaminetetraacetic acid, and sorbic acid. Other chemicals either with or witout acid functionality and having both catalytic and antimicrobial properties will be readily recognizable to those skilled in the art.

The antimicrobially active, non-woven web formed by the present invention comprises: (a) bonded cellulosic fibers; (b) a cured polymeric binder substantially uniformly distributed on the fibers, the binder being present in an amount effective to bind the cellulosic fibers; and (c) a leachable catalyst substantially uinformly ditributed on the fibers, the leachable catalyst being antimicrobial and present in an amount effective to catalyze the cross-linking of the binder.

These non-woven webs can be usd to form an antimicrobially active, wet wiper that comprises: (a) an antimicrobially active, non-woven web as defined above, and (b) a liquid in which the web is maintained in a wet condition until use.

The present invention ovecomes the numerous inherent disadvantages commonly associated with previous antimicrobially active non-woven webs and obtains the various advantages of the invention. Because the selected leachable catalyst provides the antimicrobial properties to the web, as well as catalyzing the cross-linking of the polymeric binder, there is no longer a requirement of using separate binder catalysts and antimicrobial agents in the web. By no longer requiring the presence of toxic and irritating binder catalysts, the non-woven web product of the present invention avoids leaving a toxic and irritating residue on the user's skin. Consequently, the present invention significantly advances over the state of the art and provides a non-woven web that exhibits not only the desired antimicrobial properties, but also is easier to form because the leachable catalyst serves as both a binder catalyst and an antimicrobial agent.

The foregoing and other features and advantages of the present invention will be made more apparent from the following description of the preferred embodiments.

DESCRIPTION OF THE PREFERRED EMBODIMENTS

The method of the present invention produces an antimicrobially active, non-woven web. Initially, the present method forms an unbonded cellulosic fiber web. An uncured polymeric binder is then applied throughout the unbonded cellulosic fiber web. A leachable catalyst is applied with the binder to catalyze the crosslinking of the binder during curing. The leachable catalyst possesses antimicrobial properties. After application of the uncured binder and the leachable catalyst, the binder material is cured to cross-link the binder and bind the cellulosic fibers together to form an antimicrobially active, non-woven web.

In accordance with the present invention, in the first step of the method, unbonded cellulosic fibers are formed into a web. Various techniques, such as air laying and wet laying the fibers, can be used to form the web. Although various natural and synthetic fibers known in the art can be effectively used, for economic reasons, the preferred fibers are wood pulp fibers. The wood pulp fibers can be chemically treated and pre-dried prior to air laying. Examples of wood pulp fibers include various mechanical and chemical pulp fibers, such as cedar fibers, Southern pine fibers, spruce fibers, and hemlock fibers. The particular cellulosic fibers selected to make the non-woven web depend, in part, upon the type of texture, such as soft, woolly, or fluffy, and the porosity of the web that is desired.

The weight of the fibers used to form the unbonded fiber web can vary depending upon the ultimate non-woven web that is to be produced. Typically, the weight of the fibers forming the web will vary within the range of about 5 lbs. per ream to about 60 lbs. per ream.

Various air laying techniques known in the art can be effectively used to form the unbonded cellulosic fibers. One type of apparatus for air forming cellulosic fibers is shown in U.S. Pat. No. 4,292,271 to Buob et al.

In accordance with the present invention, an uncured polymeric binder is applied throughout the unbonded cellulosic fiber web. Various polymeric binders known in the art, such as a latex binder, can be used. Acceptable latex binders include acrylate emulsions, butadiene-styrene emulsions, ethylene vinyl acetate emulsions and acrylonitrile-butadiene emulsions. An especially effective latex binder is ethylene vinyl acetate, which is sold under the trademark AIRFLEX A-106 by Air Products, Inc. of Pennsylvania. The polymeric binder can also include one or more binders selected from anionic binders, nonionic binders, and cationic binders. These binders can be used either alone or in various combinations, such as anionic and nonionic binders.

The amount of the polymeric binder that is to be applied to the fibers depends, in part, upon the type of fibers and the leachable catalyst being used in the non-woven web. Typically, the amount of the binder applied to the fibers varies within the range of about 5 to about 30%. Similarly, the amount of solids in the binder, especially a latex binder, depends, inter alia, on the weight of the cellulosic fibers in the non-woven web. Generally, latex binders having from about 5 to about 25 percent solids are used.

Of course, the skilled artisan can select the particular binder, the amount of the binder used, and the amount of solids present in the binder depending upon, in part, the type of fibers that are to be bound. The binder can be applied to the fibers by various techniques known in the art, such as spraying, foaming, or padding.

In accordance with the present invention, a leachable catalyst having antimicrobial properties is applied to the web to catalyze the cross-linking of the binder during curing. In the present invention, a catalyst is considered leachable if it substantially passes out of the non-woven web when an aqueous wetting solution is applied to the web. Any leachable catalyst that catalyzes the cross-linking of a polymeric binder and exhibits antimicrobial properties can be used in the present invention.

The particular leachable catalyst is selected, in part, based upon the binder used, the type of fibers in the web, and the degree of strength and antimicrobial activity desired in the web. Typically, different catalysts cross-link polymeric binders to varying degrees and, hence, form distinct wet strengths in the web.

The preferred leachable catalyst is an organic acid selected from the group consisting of citric acid, malic acid, ethylenediaminetetraacetic acid, and sorbic acid. These leachable organic acids are present in the web in an amount effective to catalyze the cross-linking of the binder and, preferably, are applied to the web in an amount in the range of about 0.1% to about 5% by weight of the web. Unlike previously used organic acids, these leachable organic acids are neither toxic upon ingestion nor irritating to the user's skin. Thus, antimicrobial and catalytic properties are achieved in the web without adversely affecting the surrounding environment or use of the web.

The uncured binder and the leachable organic acid are applied to the unbonded fibers in a manner that allows the binder and the leachable organic acid to be present throughout the unbonded fibrous web and, hence, substantially uniformly distributed on the fibers. The leachable organic acid is applied to the binder prior to curing the binder. However, the acid can be applied to the web simultaneously with the binder, prior to the binder, or after the binder, but before curing. As a result, substantially all of the unbonded cellulosic fibers of the web are to be contacted with the uncured binder and the leachable organic acid during this application process.

Additional chemical compounds that exhibit antimicrobial and catalytic properties, but which do not fall within the dibasic organic acid category, may also be readily used by those skilled in the art. The above noted organic acids should be considered as exemplary only.

Various binder and catalyst application methods and apparatus known in the art can be readily selected by the skilled artisan. For example, the uncured binder and the leachable organic acid can be sprayed onto unbonded fibers that have been air-laid on a foraminous support. Similarly, the uncured binder and the leachable organic acid can be contained in a bath through which the unbonded fibers pass. Other methods and apparatus include foaming and printing.

In accordance with the present invention, the binder is cured to cross-link the binder and bind the cellulosic fibers together to form an antimicrobially active, non woven-web. Various curing techniques known in the art, such as infra-red, electron beam, and ultraviolet curing, can be effectively selected and used by the skilled artisan to achieve the proper degree of binder cross-linking and cure. In part, the selected curing technique will depend upon the type of polymeric binder and catalyst used in the web.

As a result, the present invention provides an antimicrobially active, non-woven web. The non-woven web has bonded cellulosic fibers; a cured polymeric binder substantially uniformly distributed on the fibers, the binder being present in an amount effective to bind the fibers; and a leachable catalyst substantially uniformly distributed on the fibers, the leachable catalyst being antimicrobial and present in an amount effective to catalyze the cross-linking of the binder. The amount of the leachable catalyst present within the non-woven web is preferably in the range of about 0.1% to about 5% by weight of the web. The amount of the binder present within the non-woven web is preferably in the range of about 5% to about 30%.

The non-woven web of the present invention exhibits significant antimicrobial activity as the leachable catalyst, such as an organic acid, is leached from the web during the use of the web. This same catalyst that exhibits antimicrobial properties during the use of the web, also catalyzes the cross-linking of the polymeric binder while the web is being formed. Thus, the leachable catalyst performs a dual function; that is, it acts as a catalyst during the formation of the web and as an antimicrobial agent while the web is being used.

When the antimicrobially active, non-woven web of the present invention is stored in a liquid, an antimicrobial active wet wiper is achieved. The liquid, such as water, maintains the web in a wet condition until use.

The resulting wet wiper can be used to reduce the presence of a variety of bacteria and fungi. For example, the wiper can be used against microorganisms such as *Aspergillus niger, Candida albicans, Staphylococcus aureus, Pseudomonas aeruginosa,* and *Escherichia coliformia.*

Other embodiments of the invention will be apparent to one skilled in the art from a consideration of the specification or with the practice of the invention disclosed herein. It is intended that the specification be considered as exemplary only with the true scope and spirit of the invention being indicated by the claims.

What is claimed is:

1. A method for making an antimicrobially active, non-woven web comprising the steps of:
    (a) forming an unbonded cellulosic fiber web;
    (b) applying throughout the unbonded fibrous web an uncured polymeric binder;
    (c) applying a leachable catalyst to the web to catalyze the cross-linking of the binder during curing, the leachable catalyst being antimicrobial non-toxic and non-irratating and present in an amount effective to render the cured web antimicrobial; and
    (d) curing the binder to cross-link the binder and bind the fibers together to form an antimicrobially active, non-woven web.

2. The method of claim 1, wherein the polymeric binder is a latex binder.

3. The method of claim 1, wherein the polymeric binder comprises at least one binder selected from the group consisting of anionic binders, nonionic binders, and cationic binders.

4. The method of claim 1, wherein the leachable catalyst is an organic acid.

5. The method of claim 1, wherein the leachable catalyst is selected from the group of organic acids consisting of citric acid, malic acid, ethylenediaminetetraacetic acid, and sorbic acid.

6. The method of claim 1, wherein the leachable catalyst is applied to the web simultaneously with the binder.

7. The method of claim 1, wherein the amount of the leachable catalyst applied to the web is in the range of about 0.1% to about 5.0% by weight of the web.

8. A method for making an antimicrobially active, air-laid non-woven web comprising the steps of:
    (a) air laying an unbonded cellulosic fiber web;
    (b) applying throughout the unbonded cellulosic fiber web an uncured polymeric binder;
    (c) applying a leachable catalyst to the web to catalyze the cross-linking of the binder during curing, the leachable catalyst being antimicrobial and present in an amount effective to render the cured web antimicrobial and selected from the group consisting of citric acid, malic acid, ethylenediaminetetraacetic acid, and sorbic acid; and
    (d) curing the binder material to cross-link the binder and bind the cellulosic fibers together to form an antimicrobially active, air-laid, non-woven web.

9. The method of claim 8, wherein the polymeric binder is a latex binder.

10. The method of claim 8, wherein the polymeric binder comprises at least one binder selected from the group consisting of anionic binders, nonionic binders, and cationic binders.

11. The method of claim 8, wherein the amount of the leachable catalyst applied to the web is in the range of about 0.1% to about 5.0% by weight of the web.

* * * * *